(12) United States Patent
Fischer et al.

(10) Patent No.: US 7,400,982 B2
(45) Date of Patent: Jul. 15, 2008

(54) AUTOMATED GENERATION OF MULTI-DIMENSIONAL STRUCTURE ACTIVITY AND STRUCTURE PROPERTY RELATIONSHIPS

(75) Inventors: Holger Fischer, Grellingen (CH); Manfred Kansy, Freiburg (DE)

(73) Assignee: F. Hoffman-La Roche AG, Basel (CH)

( * ) Notice: Subject to any disclaimer, the term of this patent is extended or adjusted under 35 U.S.C. 154(b) by 0 days.

(21) Appl. No.: 11/495,227

(22) Filed: Jul. 28, 2006

(65) Prior Publication Data
US 2007/0027632 A1    Feb. 1, 2007

(30) Foreign Application Priority Data
Aug. 1, 2005    (EP) ................. 05016709

(51) Int. Cl.
*G06F 19/00*    (2006.01)
(52) U.S. Cl. ............... 702/19; 702/22; 702/27; 702/30; 702/32; 703/11; 707/102; 706/45

(58) Field of Classification Search ............ 702/19, 702/22, 27, 30, 32; 703/11; 707/102; 706/45
See application file for complete search history.

(56) References Cited

U.S. PATENT DOCUMENTS

| | | | | |
|---|---|---|---|---|
| 6,185,506 B1* | 2/2001 | Cramer et al. | ...... | 702/19 |
| 6,240,374 B1* | 5/2001 | Cramer et al. | ...... | 703/11 |
| 6,434,542 B1* | 8/2002 | Farmen et al. | ...... | 706/45 |
| 2003/0061186 A1* | 3/2003 | Farmen et al. | ...... | 706/20 |
| 2003/0236631 A1* | 12/2003 | Cramer et al. | ...... | 702/19 |
| 2004/0083060 A1* | 4/2004 | Church et al. | ...... | 702/19 |
| 2004/0088118 A1* | 5/2004 | Jensen et al. | ...... | 702/30 |
| 2004/0199334 A1* | 10/2004 | Kovesdi et al. | ...... | 702/27 |
| 2007/0043511 A1* | 2/2007 | Jensen et al. | ...... | 702/19 |

* cited by examiner

*Primary Examiner*—Carol S Tsai
(74) *Attorney, Agent, or Firm*—Faegre & Benson LLP

(57) ABSTRACT

The present invention relates to automated generation of multi-dimensional structure activity and structure property relationships.

4 Claims, 9 Drawing Sheets
(4 of 9 Drawing Sheet(s) Filed in Color)

Fig. 5

Model Overview

| Model | Regression Coeff. - R2 | Cross Validation - Q2 | Number of Variables |
|-------|------------------------|------------------------|---------------------|
| 15    | 0.544                  | 0.466                  | 5                   |
| 16    | 0.727                  | 0.586                  | 4                   |
| 17    | 0.674                  | 0.558                  | 3                   |
| 18    | 0.635                  | 0.595                  | 2                   |
| 19    | 0.638                  | 0.609                  | 1                   |

General Remarks:
- The higher R2 and Q2 the "better" the model.
- The lower the Number of Variables the easier the interpretation of the model.
Additional calculations are performed. Please wait...

| Model | Model Summary | Transfer Plots to Spotfire | Validate the Model | | Keep the Model |
|-------|---------------|-----------------------------|---------------------|---|-----------------|
| 15    |               | ⦿ Regression  ○ Coefficients | Predict List | Predict Single | Not yet available |
| 16    |               | ⦿ Regression  ○ Coefficients | Predict List | Predict Single | Not yet available |
| 17    |               | ⦿ Regression  ○ Coefficients | Predict List | Predict Single | Not yet available |
| 18    |               | ⦿ Regression  ○ Coefficients | Predict List | Predict Single | Not yet available |
| 19    |               | ⦿ Regression  ○ Coefficients | Predict List | Predict Single | Not yet available |

See List with Abbreviations    Interpretation Coefficients

Fig. 6

| Structure | pGLYT1 | NHP_60 | phERG | Mdia_10 | Ranking Score |
|---|---|---|---|---|---|
| Chemistry 12 | 0,222 | 0,14 | 0,126 | 0,122 | 0,528 |
| Chemistry 13 | 0,222 | 0,14 | 0,126 | 0,122 | 0,528 |
| Chemistry 14 | 0,222 | 0,14 | 0,126 | 0,122 | 0,528 |
| Chemistry 15 | 0,18 | 0,132 | 0,107 | 0,143 | 0,514 |
| Chemistry 16 | 0,18 | 0,132 | 0,107 | 0,143 | 0,514 |
| Chemistry 17 | 0,18 | 0,132 | 0,107 | 0,143 | 0,514 |
| Chemistry 21 | 0,192 | 0,15 | 0,054 | 0,134 | 0,488 |
| Chemistry 22 | 0,192 | 0,15 | 0,054 | 0,134 | 0,488 |
| Chemistry 23 | 0,192 | 0,15 | 0,054 | 0,134 | 0,488 |
| Chemistry 41 | 0,074 | 0,121 | 0,072 | 0,169 | 0,483 |
| Chemistry 42 | 0,074 | 0,121 | 0,072 | 0,169 | 0,483 |
| Chemistry 43 | 0,074 | 0,121 | 0,072 | 0,169 | 0,483 |
| Chemistry 27 | 0,15 | 0,142 | 0,035 | 0,155 | 0,474 |
| Chemistry 28 | 0,15 | 0,142 | 0,035 | 0,155 | 0,474 |
| Chemistry 29 | 0,15 | 0,142 | 0,035 | 0,155 | 0,474 |
| Chemistry 30 | 0,118 | 0,112 | 0,077 | 0,171 | 0,472 |
| Chemistry 31 | 0,118 | 0,112 | 0,077 | 0,171 | 0,472 |
| Chemistry 32 | 0,118 | 0,112 | 0,077 | 0,171 | 0,472 |
| Chemistry 38 | 0,069 | 0,096 | 0,112 | 0,162 | 0,466 |
| Chemistry 39 | 0,069 | 0,096 | 0,112 | 0,162 | 0,466 |
| Chemistry 40 | 0,069 | 0,096 | 0,112 | 0,162 | 0,466 |

Fig. 9

AUTOMATED GENERATION OF MULTI-DIMENSIONAL STRUCTURE ACTIVITY AND STRUCTURE PROPERTY RELATIONSHIPS

REFERENCE TO RELATED APPLICATION

This application claims priority to European Patent Application 05 01 6709.7 filed Aug. 1, 2005, which is hereby incorporated by reference.

The present invention relates to automated generation of multi-dimensional structure activity and structure property relationships.

BACKGROUND

With the development and implementation of High-Throughput Systems (HTS) the pharmaceutical industry faces more and more the problem of an adequate analysis of the obtained data. In particular, there is a need for conversion of information derived from multi-dimensional data matrixes into structural chemical information.

It is the object of the present invention to provide a method for automatic finding of potential correlations in complex data matrixes. It is a further object of the present invention to provide a user with chemical structural or chemical property information about the latent multidimensional cohesions. These objects are achieved with the features of the claims.

According to a first aspect, the present invention provides a method directed to the analysis of the effect of a structural fragment of a chemical structure on at least one biological descriptor.

The method according to the first aspect comprises the steps of:
A) providing data about at least one set of chemical structures;
B) providing data about at least one biological descriptor;
C) calculating structural fragments for each chemical structure;
D) associating said structural fragments for each chemical structure with said biological descriptor data in order to obtain a data matrix;
E) analysing the data in said data matrix with a view on the effect of a fragment of each chemical structure on said biological descriptor; and
F) visualizing the result of said analysis.

Preferably, in step e), each of the fragments calculated in step c) is linked to the biological descriptor data. This is preferably done using a partial-least-square method. Alternatively, neural networks, multiple linear regression, or support vector machines are used.

In step d) of the method of the first aspect of the present invention, the fragments are preferably selected on the basis of a predefined scaffold structure. In this context, the term "predefined scaffold structure" means a basic structure being selected by the user of the method, for example a chemist, and the fragments of such basic structure are varied. Predefined scaffolds structures can also be identified by an automated search for the most common chemical substructure. As an alternative, the present method encompasses that in step d) the fragments are generated on the basis of molecular fragments.

According to a preferred embodiment of the method according to the first aspect, step d) is followed by the step of calculating physico-chemical properties for each fragment. Preferably, step e) analyses the data in the data matrix with a view on the effect of a fragment and its physico-chemical properties on the biological descriptor. Each physico-chemical property of each fragment is preferably linked to the biological descriptor data.

According to a second aspect, the present invention provides a method directed to the analysis of the effect of physico-chemical properties of a chemical structure on at least one biological descriptor.

The method according to the second aspect comprises the steps of:
A) providing data about at least one set of chemical structures;
B) providing data about one biological descriptor;
C) calculating physico-chemical properties of each chemical structure;
D) associating said physico-chemical properties of each chemical structure with said biological descriptor data in order to obtain a data matrix;
E) analysing the data in said data matrix with a view on the effect of each physico-chemical property of each chemical structure on said biological descriptor; and
F) visualizing the result of said analysis.

Preferably, in step E), each physico-chemical property of each chemical structure is linked to said biological descriptor data.

The physico-chemical properties of said chemical structures or fragments are preferably selected from the group comprising hydrophilicity, hydrophobicity, electricity, shape, and amphiphilicity. However, the present invention is not limited to these properties. In this context, reference is made to Todeschini, Roberto Consonni, Viviana, Handbook of Molecular Descriptors, Methods and Principles in Medical Chemistry Vol. 11, WILEY-VCH, 2000.

According to the methods of the first and second aspect, the biological descriptor data are independently selected from pharmacological, toxicological, and pharmacokinetic data. For example, the at least one biological descriptor is selected from the group comprising descriptors relating to receptor activity, selectivity, bio-availability, and in vivo activity. However, these biological descriptors are only examples of a variety of descriptors that are preferably used in the present invention. Further examples of potential descriptors are given below.

Like in the method of the first aspect, the second aspect of the present invention preferably uses a partial-least-square method for analysing the data in the data matrix with a view on the effect of each physico-chemical property of each chemical structure on the biological descriptor (step E)). Alternatively, as mentioned above, neural networks, multiple linear regression, or support vector machines are used.

In the following, preferred features of the first and the second aspect are described.

Preferably, the visualisation of the results is made as a two-dimensional pattern or matrix dependent on the chemical structure and the biological descriptor(s), wherein the pattern represents a positive or negative effect of each of the fragments or each physico-chemical property on the biological descriptor(s). More preferably, the portions of the pattern representing a positive effect of each of the fragments or each physico-chemical property on the biological descriptor are highlighted different from the portions of the pattern representing a negative effect of each of the fragments or each physico-chemical property on the biological descriptor(s). Most preferably, the different portions are coloured differently.

The methods of the first or second aspect may further comprise the step of validating the result with an independent data set.

According to a further preferred embodiment, the methods comprise the step of automatically generating new molecules with favourable multi-dimensional profiles.

In the following, the method steps of the present invention are described in more detail. The methods of the present invention start with the data input (chemical structures and one or more biological descriptors with its activities). Preferably, at least three chemical structures, more preferably five, are provided as input data. Furthermore, the biological parameter or descriptor is provided as input data, and the activities of this descriptor. Preferably three activities are input, more preferably five activities for each biological descriptor.

Based on these input data, according to the method of the first aspect of the present invention, the fragments of the chemical structures are varied in order to obtain various sets for the data analysis, and the PLS is performed on these various data sets. As an example, the following equation is used according to the present invention:

$$Y = a \cdot \text{Fragment}A + b \cdot \text{Fragment}B + \ldots + x \cdot \text{Fragment}N + Z \quad (1)$$

wherein Y represents the activity value of the biological descriptor being provided as input, FragmentA through FragmentN represent the fragments that are considered, a through x are coefficients, and z is a constant. Each parameter FragmentI is either 1 or 0 dependent on whether the fragment is considered in the particular model or not.

This general formula shows that in principle a plurality of fragments can be considered for the data analysis. However, in practice, it is desirable to have only a few number of fragments in order to keep the number of necessary calculations at a reasonable minimum, and more importantly to ensure that the results can be interpreted and that the influence and effect of each fragment can be determined by the user.

According to the method of the second aspect of the present invention, again based on these input data, the physico-chemical properties of the chemical structures are for example calculated or read from a database, and the PLS is performed on these various models. As an example, the following formula is used according to the present invention:

$$Y = a \cdot \text{property}1 + b \cdot \text{property}2 + \ldots + x \cdot \text{property}N + z \quad (2)$$

wherein Y represents the activity value of the biological descriptor being provided as input, property1 through propertyN represent the physico-chemical properties that are considered, a through x are coefficients, and z is a constant. This general formula shows that in principle a plurality of properties can be considered for the data analysis. However, in practice, it is desirable to have only a few number of properties in order to keep the number of necessary calculations at a reasonable minimum, and more importantly to ensure that the results can be interpreted and that the influence and effect of each property can be determined.

Typically, equations (1) and (2) are solved for all activities provided as input data, i.e. the unknown coefficients and constant of these equations are calculated on the basis of the available equations, one for each activity.

Preferably, the coefficients are normalized and centralized so that they are comparable with each other (because they may have different dimensions).

According to the present invention, three aspects are an indication for the quality of the model (i.e. three quality parameters). First, the variable importance, i.e., the relevance of the fragment or physico-chemical property. Secondly, the absolute value of the calculated coefficients (in case PLS is used for the data analysis). If a calculated coefficient (of above equations (1) or (2)) is small, the effect of the associated variable is only small, even if this variable is an important one. Thirdly, the number of variables (fragments or physico-chemical properties) that are used. Basically, as mentioned above, the number of variables should be as small as possible in order to have a model that is interpretable by the user.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

The patent or application file contains at least one drawing executed in color. Copies of this patent or patent application publication with color drawing(s) will be provided by the Office upon request and payment of the necessary fee.

The present invention will now be described in more detail with reference to the accompanying drawings, in which

FIG. 5 shows a screenshot of an input mask of a computer implementation of the present invention;

FIG. 6 shows a screenshot of the results calculated by the methods of the present invention;

FIG. 9 shows an example of ranking list with newly generated molecules.

DETAILED DESCRIPTION

Figure 1:
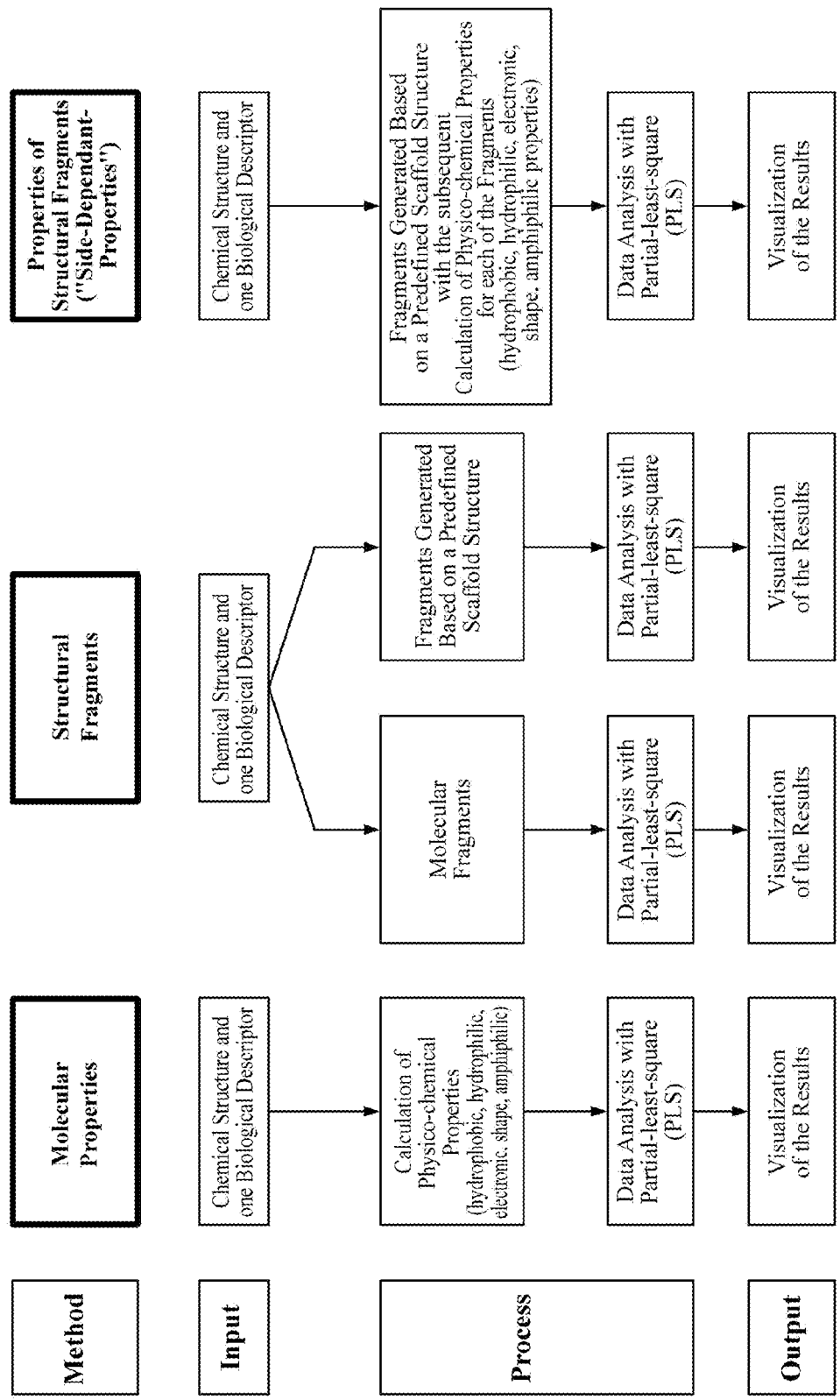
FIG. 1 shows three flow diagrams which represent the methods according to the first and the second aspects of the present invention as well as a combination of both aspects.

FIG. 1 shows the principles of the present invention in form of flow diagrams. The flow diagram in the middle of FIG. 1 shows the method according to the first aspect of the present invention. According to this method, data about at least one set of chemical structures is provided as input data. Such chemical structures are typically identified by respective codes of the provider of such structure data, for example a sequence of letters and numbers, and these codes are provided as input data. The specific data about the chemical structures are provided for example in a database, and with the input code the chemical structures can be distinguished and accessed at the database. Furthermore, data about at least one biological descriptor is provided as further input data. Based on these input data, two alternative embodiments are encompassed by this method. These two alternative embodiments are represented by the two branches of the middle flow diagram of FIG. 1. According to the left branch, molecular fragments are selected and calculated from the chemical structures. In the next step, a data analysis is performed in order to associate the molecular fragments for each chemical structure with the biological descriptor data in order to obtain a data matrix. As shown in FIG. 1, a partial-least-square (PLS) method is preferred for the data analysis. Finally, the results are visualised, as will be described in more detail below.

In the alternative embodiment, instead of molecular fragments, fragments selected on the basis of a predefined scaffold structure are used. Again, this step is followed by a data analysis, preferably partial-least-square method. In the last step shown in FIG. 1, the results are visualized.

FIG. 1 also shows in its left flow diagram the method according to the second aspect of the present invention. According to this aspect, data about at least one set of chemical structures and data about one biological descriptor are provided as input data. On the basis of these input data, physico-chemical properties of each chemical structure are calculated. The respective box in FIG. 1 gives some examples for these properties, such as hydrophobicity, hydrophilicity, electricity, shape, amphiphilicity etc. Again, this step is followed by a data analysis, preferably partial-least-square method. In the last step shown in FIG. 1, the results are visualized.

For the calculation of the physico-chemical properties, standard tools can be used. Such standard tools are, for example, Msrfv1 available from GMD (Gerber Molecular Design, Amgen, Switzerland); 1D-prop or ClogP available from Daylight Inc., Los Altos Mission Viejo, Calif., USA, pKaDB available from ACDLabs (Advanced Chemistry Development, Inc.), Toronto, Ontario M5H 3V9, Canada, or CAFCA available from Roche.

The PLS preferably uses C-libraries from Umetrics, Inc., Umeå, Sweden.

A combination of both aspects is shown in the right flow diagram of FIG. 1. Based on the input data (data about at least one set of chemical structures and data about at least one biological descriptor), fragments are selected based on a predefined scaffold structure, and subsequently the physico-chemical properties are calculated for each of the fragments. PLS data analysis is again followed by a visualisation of the results.

Figure 2:
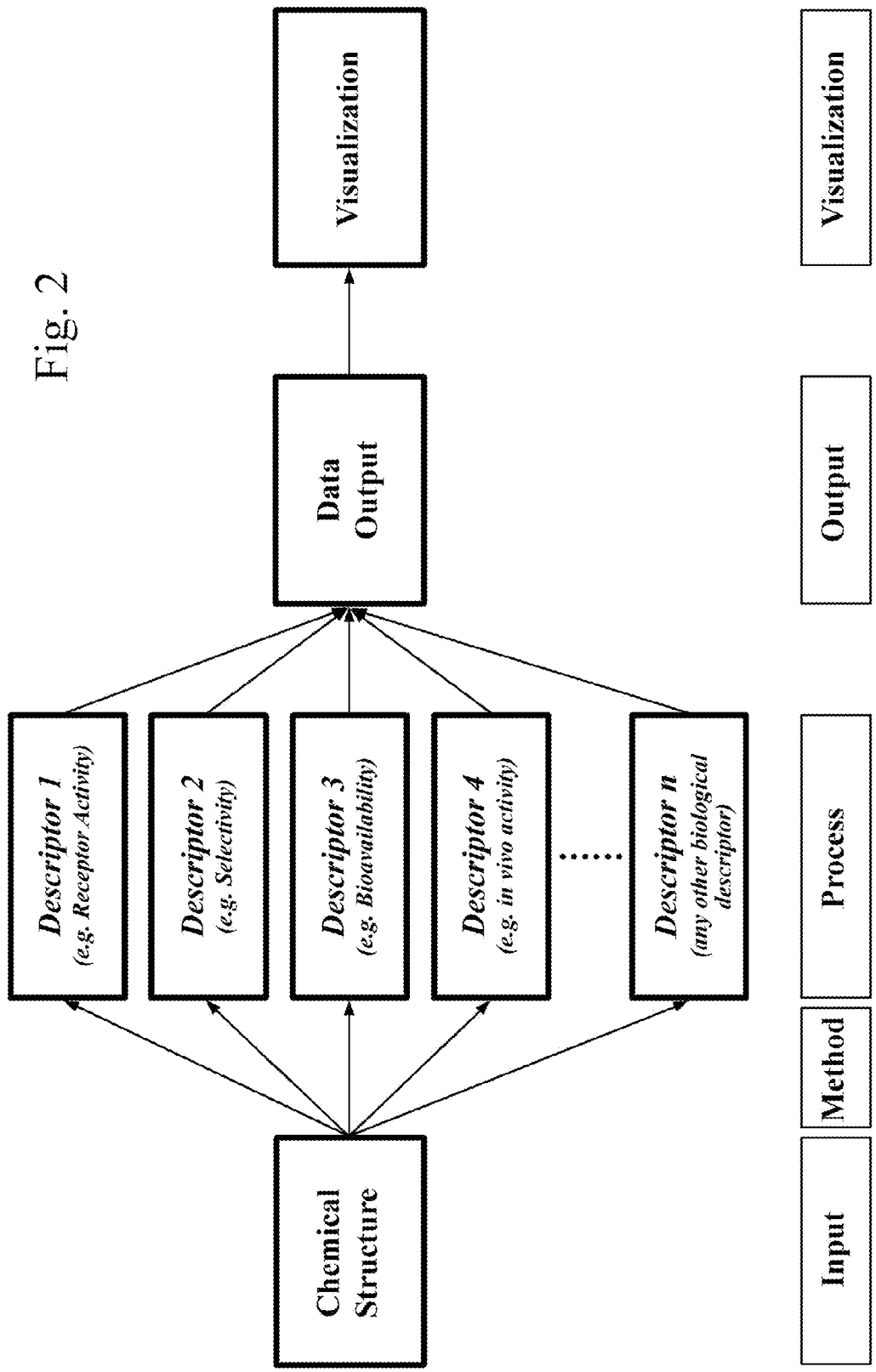
FIG. 2 shows one process step of the first aspect of the present invention in more detail.

As already described above, the method according to the first aspect of the present invention as well as the method combining both aspects can be used for the analysis of multiple biological descriptors. This is shown in schematic form in FIG. 2. In principle, n biological descriptors can be used for the analysis. The examples given in FIG. 2 are receptor activity, selectivity, bioavailability, and in-vivo activity.

Figure 3:
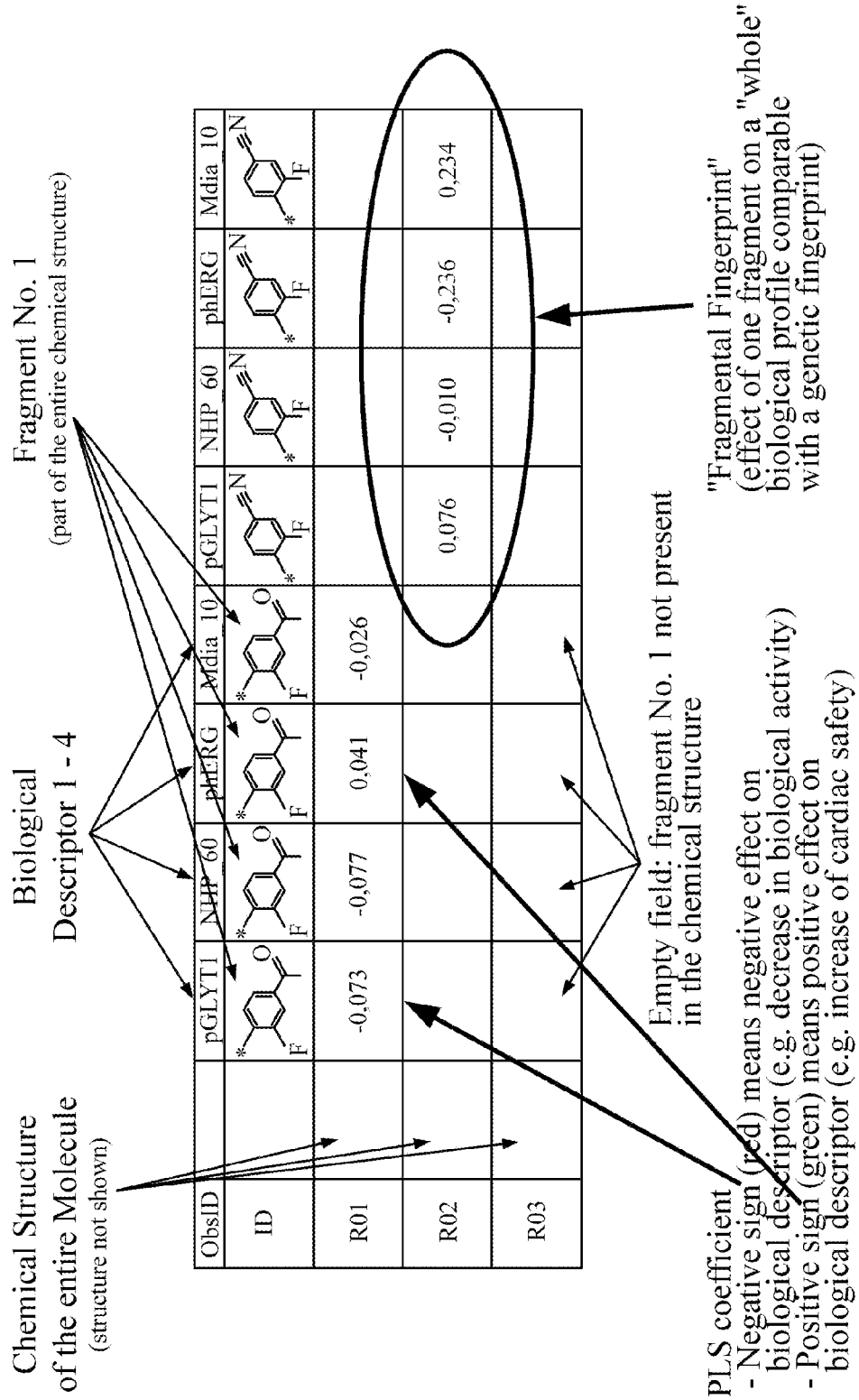
FIG. 3 shows an exemplary visualisation of the results of the method of the first aspect of the present invention.

An example of the visualisation of the results of the method using more than one biological descriptor is shown in FIG. 3.

The table or matrix shown in FIG. 3 shows in its second line the different fragments used for the analysis. As shown in FIG. 3, the part of the chemical structure can be explicitly shown. In the example shown in FIG. 3, four different biological descriptors are used which are mentioned in the first line (pGLYT1, NHP_60, phERG, Mdia_10). For this reason, blocks or groups are formed in the matrix. In more detail, the third to sixth columns relate to the first fragment with varying descriptor, and the next four columns relate to the next fragment with varying the same descriptors.

Preferably, the second column shows the chemical structure of the entire molecule. However, for reasons of simplicity, these entire molecules are not shown in FIG. 3.

The results of the data analysis are shown in the various columns under the fragments. That is, in case PLS is used for data analysis, the results of the PLS, i.e., the PLS coefficients are listed in the matrix for each fragment, descriptor, and molecule. In addition to the mere listing of the PLS coefficients, the coefficients are preferably individually highlighted so that the user can easily see the differences in the results, namely the different effect of the fragment on the biological descriptor. For example, a matrix field having a coefficient with a negative sign is highlighted in red (dark grey in black/white picture) representing a negative effect on the biological descriptor (for example, decrease in biological activity). On the other hand, a positive sign is additionally highlighted in a different way, for example in a different colour. In the example shown in FIG. 3, a field highlighted in green (light grey in a black/white picture) means a positive effect on the biological descriptor (e.g., increase in cardiac safety).

Empty fields in the matrix mean that the respective fragment is not present in the tested chemical structure.

Furthermore, each group of fields in one matrix line for a specific fragment represents according to the present invention a "fragmental fingerprint". A fragmental fingerprint represents the effect of one fragment on a "whole" biological profile comparable with a genetic fingerprint. This will be described in more detail below with reference to FIG. 8.

Figure 4:
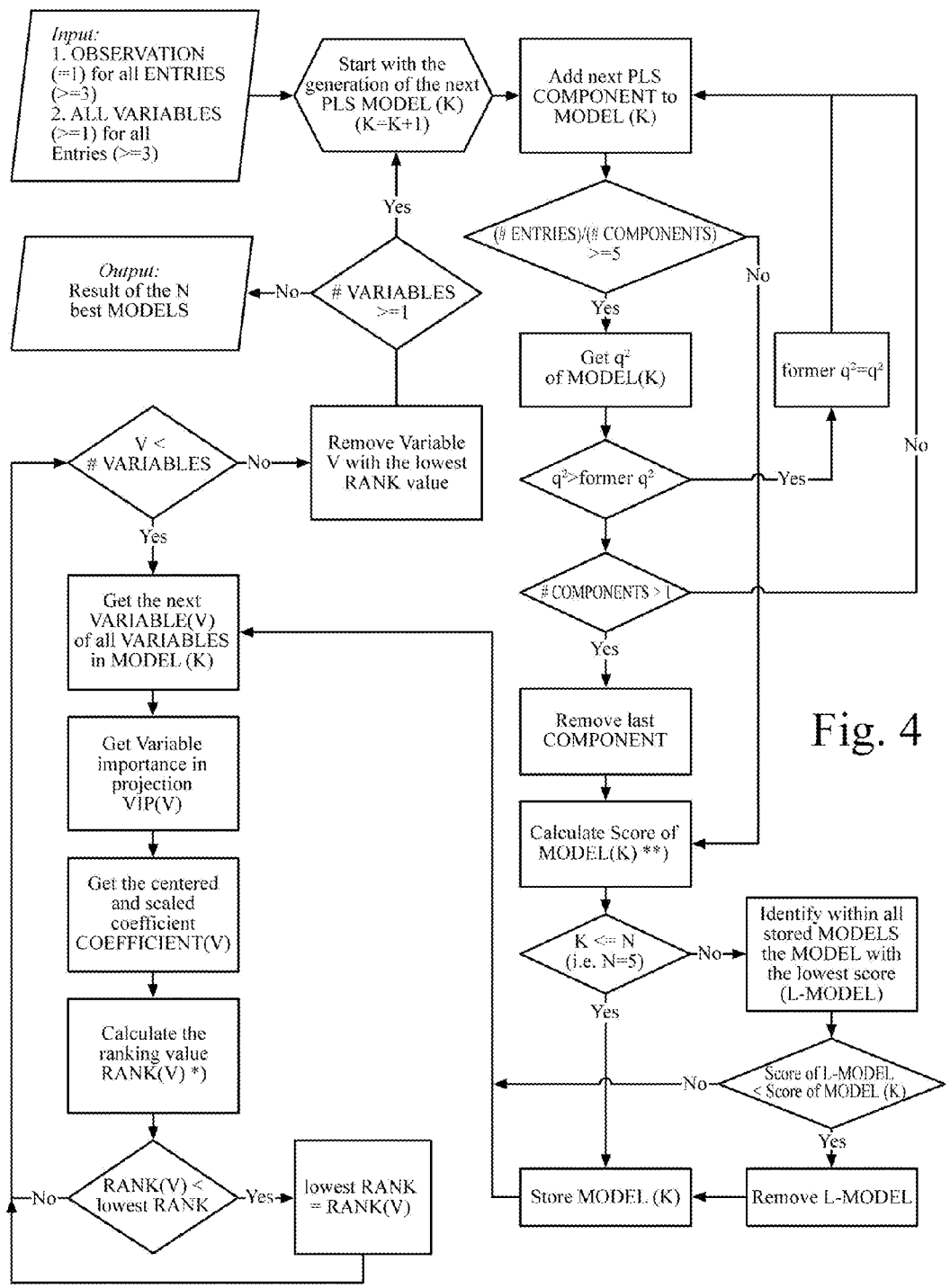
FIG. 4 shows a detailed flow chart for the selection of models according to the present invention.

FIG. 4 shows a detailed flow chart for the selection of models according to the present invention, preferably using PLS. The following table describes the abbreviations used in the flow chart.

TABLE 1

List of abbreviations

| Abbreviation | Description |
|---|---|
| # | Number of . . . |
| COEFFICIENT(S) | Centered and scaled coefficient of a VARIABLE from a PLS analysis |
| COMPONENT | Principal component calculated by PLS |
| ENTRIES | Individual entries with one OBSERVATION and multiple VARIABLES (minimal number of 3 ENTRIES) are required) |
| K | Sequence number for the generated MODELS |
| L-MODEL | MODEL with the lowest score in the stock |
| MODEL | Model generated with Partial-Least Square (PLS) analysis |
| MODEL SCORE | Scoring value of the individual model. Specifies the performance of the MODEL (K). Various calculations possible. |
| N | Number of the best MODELS which should be displayed in the output |
| OBSERVATION | Any Biological Observation (Y-values) from the fields of in vitro/in vivo pharmacodynamic, in vitro/in vivo pharmacokinetic, in vitro/in vivo toxicology, in vitro/in vivo safety or any physico-chemical parameters. Namely, absorption, bioavailability, distribution, clearance, stability, excretion, blood-brain barrier permeation, cerebro-spinal fluid (CSF) levels, affinity to transporters (i.e. P-gp, OAT, OCT, . . . ), drug-drug interaction (DDI), microsomal stability, hepatocyte clearance, enzyme activity, enzyme selectivity, GPCR activity, GPCR selectivity, in vivo activity, in vivo selectivity, ion channel interaction, phospholipidosis, AMES activity, genotoxicity, carcinogenicity, teratogenicity, hepatotoxicity, phototoxicity, permeability, membrane binding, logP, HLB, solubility in different media, . . . |
| PLS | Partial-Least Square (PLS) analysis |
| RANK | Ranking values calculated by the specified equation |
| V | Sequence number for VARIABLES of the MODEL (K) |
| #V | Number of all VARIABLES in MODEL (K) |
| VARIABLE(S) | Collection of user defined descriptors of the ENTRY (minimal number of 1 is required) |
| VIP | Variable importance of projection |

As can be taken from the flow chart of FIG. 4, OBSERVATIONS are input. Possible biological observations comprise any biological observation (Y-values) from the fieleds of in vitro/in vivo pharmacodynamic, in vitro/in vivo pharmacokinetic, in vitro/in vivo toxicology, in vitro/in vivo safety or any physico-chemical paremeters such as absorption, bioavailability, distribution, clearance, stability, excretion, blood-brain barrier permeation, cerebro-spinal fluid (CSF) levels, affinity to transporters (i.e., P-gp, OAT, OCT etc.), drug-drug interaction (DDI), microsomal stability, hepatocyte clearance, enzyme activity, enzyme selectivity, GPCR activity, GPCR selectivity, in vivo activity, in vivo selectivity, ion channel interaction, phospholipidosis, AMES activity, genotoxicity, carcinogenicity, teratogenicity, hepatotoxicity, phototoxicity, permeability, membrane binding, logP, HLP, solubility in different media, etc.

Furthermore, according to the preferred embodiment shown in FIG. 4, at least three ENTRIES such as chemical structures, and at least one descriptor is provided as input data. Based on these input data, data analysis with PLS is performed, and the results of the N best models is finally output to the user. N is an integer number selected by the user.

An example of an input table is shown in the following:

TABLE 2

| | Input data | | | | | |
|---|---|---|---|---|---|---|
| ID | Biological observation | Variable 1 | Variable 2 | Variable 3 | Variable 4 | ... |
| Molecule 1 | | | | | | |
| Molecule 2 | | | | | | |
| Molecule 3 | | | | | | |
| Molecule 4 | | | | | | |
| Molecule 5 | | | | | | |
| ... | | | | | | |

Figure 5:
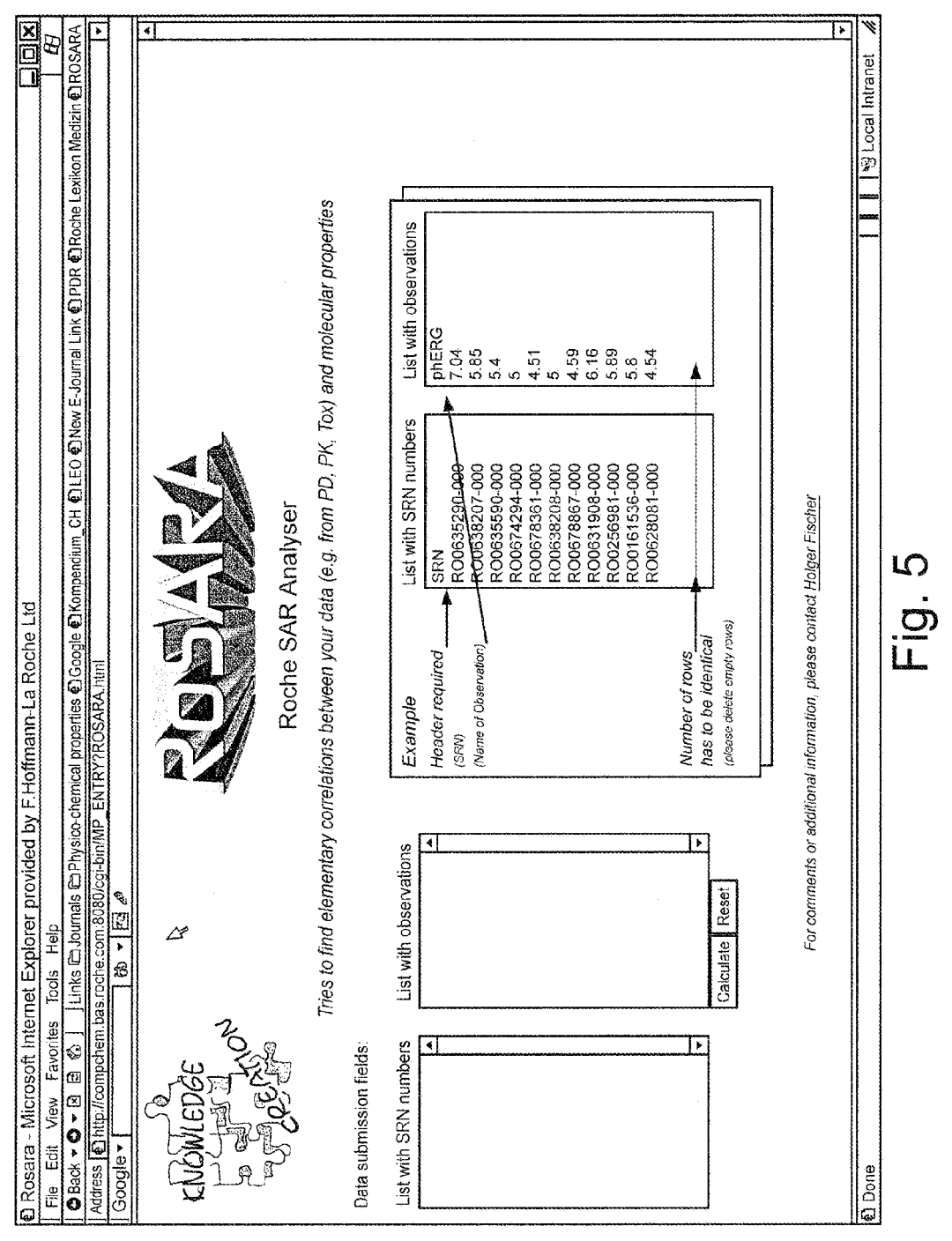

FIG. 5 shows a screenshot of an input mask of a computer implementation of the present invention. In the left part of the screen, the two input or data submission fields are shown. In the left submission field, the codes of the chemical structure are input. Preferably, at least three chemical structures, more preferably five, are input. Furthermore, the biological parameter or descriptor is input in the left one of the two data submission fields, and the activities of this descriptor. Preferably three activities are input, more preferably five activities. The right part of the screenshot of FIG. 5 shows an example where the codes of eleven chemical structures are input as well as eleven different activities for the descriptor pHERG.

Based on these input data, the physico-chemical properties are for example calculated or read from a database, and the PLS is performed on various models. The results of the data analysis are shown in FIG. 6. For example, if only two physico-chemical properties are considered (such as ClogP and Surface), above equation (2) is as follows:

$$Y = a \cdot clogP + b \cdot surface + c$$

If the first value for the biological descriptor shown in FIG. 5 is used, and assuming clogP=3.0 and Surface=345 Å$^2$ (as an example), equation (2) would read:

$$7.04 = a \cdot 3.0 + b \cdot 345 + c$$

On the basis of this and other equations for other activity values and parameter values, a, b, and c need to be determined.

FIG. 6 shows in its upper table the results for five different models, i.e. numbers 15 through 19 listed in this table. These models are distinguished from each other by the number of variables (i.e., physico-chemical properties) that are considered in the PLS (see most right column in this table). The second and third columns of this table show the calculated regression coefficients R2 and the calculated cross validation values Q2 of the PLS. In order to allow the user to easily identify the best results, it is preferred that these are highlighted different from the other less preferable results. In the example show in FIG. 6, the regression coefficient R2 for model 16 0.727 is highlighted. Furthermore, the cross validation value Q2 for model 19 0.609 is highlighted. The higher R2 and Q2, the better the selected model. In the last column, models 18 and 19 are highlighted because they are preferred because the small numbers of variables used. The more variables are used, the more difficult it is for the user to identify those parameters that are more important than others, and the easier the model can be interpreted by the user.

In addition to the mere listing of numbers in a table, FIG. 6 shows that graphical results are also available according to a preferred embodiment of the present invention. Model summaries in form of different graphical representations can be displayed (see second and third column in the lower table of FIG. 6), and regression plots and coefficient plots can be displayed.

Figure 7:
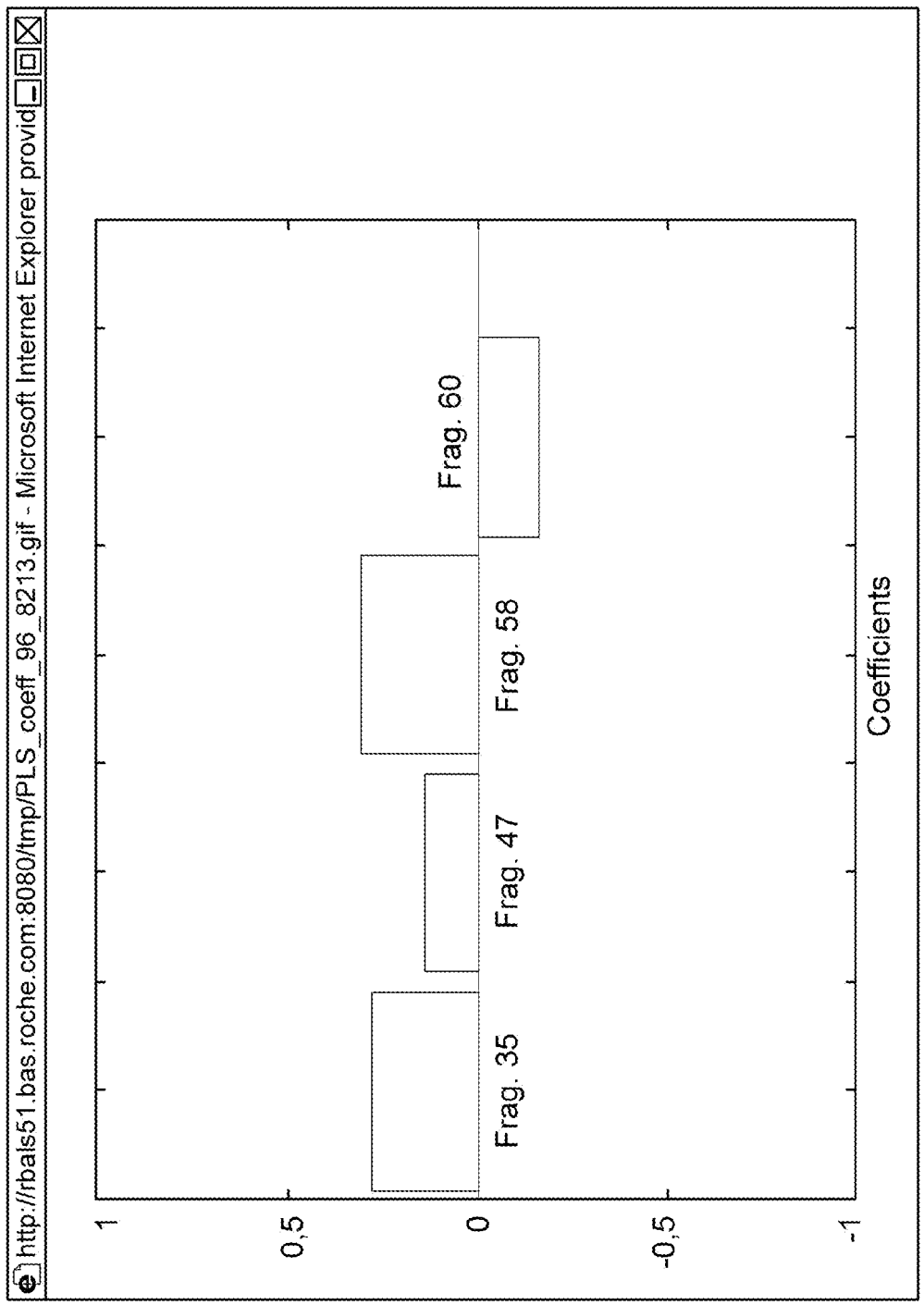
FIG. 7 shows an exemplary screenshot of a coefficient plot calculated with the present invention.

An exemplary coefficient plot is shown in FIG. 7. In this example, which is based on the method according to the first aspect of the present invention, four fragments were used, and the calculated coefficients for these are shown in FIG. 7. For the first three (Frag 35, Frag 47, and Frag 58) the coefficients are positive, and for the last parameter (Frag 60) the calculated coefficient is negative.

Figure 8:
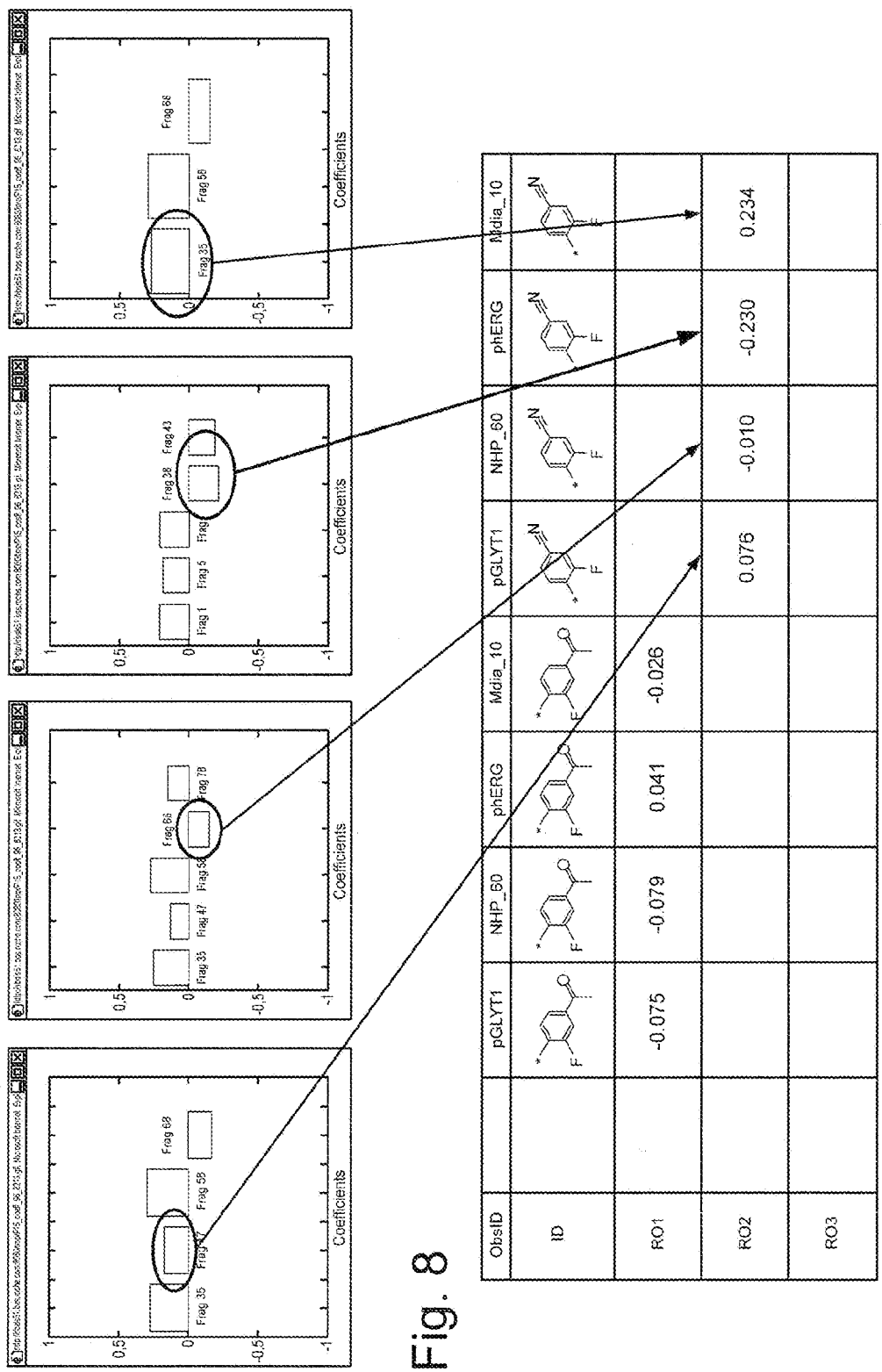
FIG. 8 shows how a fragmental fingerprint can be obtained with the present invention.

The relationship between the calculated coefficients for the different fragments and the data matrix (see FIG. 3) is clearly shown in FIG. 8. Here, four screenshots are shown. The most left screenshot is the one shown in more detail in FIG. 7, i.e., coefficients for fragments Frag 35, Frag 47, Frag 58, and Frag 60. The next screenshot to the right shows coefficients for a model calculated based on fragments Frag 35, Frag 47, Frag 58, Frag 60, and Frag 70. The further right screenshot shows coefficients for Frag 1, Frag 5, Frag 6, Frag 38, and Frag 43. Finally, the most right screenshot shows calculated coefficients for Frag 35, Frag 58, and Frag 60. as can be clearly seen from the different coefficient values, the effect of these fragments differs.

The calculated coefficients for the considered fragments are input in the data matrix as also shown in FIG. 8. The right group of four coefficients 0.076, −0.10, −0.230, and 0.234 relate to fragments Frag 47, Frag 60, Frag 38, and Frag 35.

As shown in FIG. 9, the method according to the present invention further comprises the step of ranking the results. FIG. 9 shows a ranking score for 21 structures enumerated "Chemistry 12" through "Chemistry 40". For these structures, the calculated values for the descriptors pGLYT1, NHP_60, phERG, and Mdia_10, as examples, are listed.

Preferably, the data in this data matrix obtained for each chemical structure are summed up to obtain the ranking of this chemical structure, for example by the formula:

$$\text{Rancing\_Score} = a \cdot pGLYT + b \cdot NHP\_60 + c \cdot phERG + d \cdot Mdia\_10$$

with the weights being a=1, b=1, c=1, and d=1. The weights are not fixed and can be adapted to any values.

Thus, for the newly generated molecules "Chemistry 12" through "Chemistry 40" a ranking is obtained according to the present invention.

The invention is further set forth in the claims listed below. This invention may take on various modifications and alterations without departing from the spirit and scope thereof. In describing embodiments of the invention, specific terminology is used for the sake of clarity. The invention, however, is not intended to be limited to the specific terms so selected, and it is to be understood that each term so selected includes all technical equivalents that operate similarly.

The invention claimed is:

1. A method comprising the steps of:
   a) providing data about at least one set of chemical structures;
   b) providing data about one biological descriptor;
   c) calculating physico-chemical properties of each chemical structure;
   d) associating said physico-chemical properties of each chemical structure with said biological descriptor data in order to obtain a data matrix;
   e) analysing the data in said data matrix with a view on the effect of each physico-chemical property of each chemical structure on said biological descriptor;
   f) visualizing the result of said analysis;
   g) generating new molecules with favourable multi-dimensional profiles;
   wherein in step e) a partial-least-square method is used; and wherein in step f) the results are visualized as a two-dimensional pattern dependent on the chemical structure and the biological descriptor(s), said pattern representing a positive or negative effect of each of the fragments or each physico-chemical property on said biological descriptor(s).

2. The method of claim 1 wherein the portions of said pattern representing a positive effect of each of the fragments or each physico-chemical property on said biological descriptor are highlighted different from the portions of said pattern representing a negative effect of each of the fragments or each physico-chemical property on said biological descriptor(s).

3. The method of claim 2 wherein the different portions are coloured differently.

4. A method comprising the steps of:
   a) providing data about at least one set of chemical structures;
   b) providing data about one biological descriptor;
   c) calculating physico-chemical properties of each chemical structure;
   d) associating said physico-chemical properties of each chemical structure with said biological descriptor data in order to obtain a data matrix;
   e) analysing the data in said data matrix using a partial-least-square method with a view on the effect of each physico-chemical property of each chemical structure on said biological descriptor;
   f) visualizing the result of said analysis as a two-dimensional pattern dependent on the chemical structure and the biological descriptor(s), wherein said pattern represents a positive or negative effect of each of the fragments or each physico-chemical property on said biological descriptor(s) and wherein the portions of said pattern representing a positive effect of each of the fragments or each physico-chemical property on said biological descriptor(s) are highlighted different from the portions of said pattern representing a negative effect of each of the fragments or each physico-chemical property on said biological descriptor(s); and
   g) generating new molecules with favourable multi-dimensional profiles.

* * * * *